US006913622B2

(12) United States Patent
Gjunter

(10) Patent No.: US 6,913,622 B2
(45) Date of Patent: Jul. 5, 2005

(54) ARTIFICIAL DISC

(75) Inventor: Victor Eduardovich Gjunter, Tomsk (RU)

(73) Assignee: Biorthex Inc., Quebec (CA)

(*) Notice: Subject to any disclaimer, the term of this patent is extended or adjusted under 35 U.S.C. 154(b) by 0 days.

(21) Appl. No.: 10/399,020

(22) PCT Filed: Oct. 12, 2001

(86) PCT No.: PCT/CA01/01441

§ 371 (c)(1),
(2), (4) Date: Oct. 10, 2003

(87) PCT Pub. No.: WO02/30336

PCT Pub. Date: Apr. 18, 2002

(65) Prior Publication Data

US 2004/0049282 A1 Mar. 11, 2004

(30) Foreign Application Priority Data

Oct. 12, 2000 (CA) .............................................. 2323252

(51) Int. Cl.$^7$ .................................................. A61F 2/44
(52) U.S. Cl. ................................. 623/17.16; 623/23.54
(58) Field of Search ........................... 623/17.11–17.16, 623/23.53–23.55, 11.11, 16.11; 606/60–61, 69–71; 128/898, 848, 200.24, 205.19, 202.12, 19, 24, 807, DIG. 23; 600/21, 22; 602/18, 1.3, 902

(56) References Cited

U.S. PATENT DOCUMENTS

| | | | | | |
|---|---|---|---|---|---|
| 3,852,045 | A | * | 12/1974 | Wheeler et al. | 428/566 |
| 4,693,721 | A | * | 9/1987 | Ducheyne | 623/23.54 |
| 4,932,969 | A | * | 6/1990 | Frey et al. | 623/17.12 |
| 5,171,280 | A | * | 12/1992 | Baumgartner | 623/17.12 |
| 5,306,310 | A | | 4/1994 | Siebels | |
| 5,380,328 | A | * | 1/1995 | Morgan | 606/70 |
| 5,716,416 | A | * | 2/1998 | Lin | 623/17.16 |
| 5,919,235 | A | * | 7/1999 | Husson et al. | 623/17.16 |
| 6,019,793 | A | * | 2/2000 | Perren et al. | 623/17.16 |
| 6,206,924 | B1 | * | 3/2001 | Timm | 623/17.16 |
| 6,482,235 | B1 | * | 11/2002 | Lambrecht et al. | 623/17.16 |
| 6,488,710 | B2 | * | 12/2002 | Besselink | 623/17.15 |
| 6,673,075 | B2 | * | 1/2004 | Santilli | 606/61 |

FOREIGN PATENT DOCUMENTS

| | | |
|---|---|---|
| EP | 0 621 018 | 10/1994 |
| SU | 1 526 675 | 12/1989 |
| WO | WO 98/38918 | 9/1998 |
| WO | WO 99/34845 | 7/1999 |

* cited by examiner

Primary Examiner—David J. Isabella
(74) Attorney, Agent, or Firm—Bachman & LaPointe, P.C.

(57) ABSTRACT

An implant device for surgical treatment of spinal disc damage or injury is formed as a resilient body comprising porous TiNi; the body is internally mobile such that it resiliently expands and contracts in response to variation in forces applied externally on the body.

19 Claims, 3 Drawing Sheets

ARTIFICIAL DISC

TECHNICAL FIELD

The invention relates to a medical implant device for use in the surgery of the spine.

BACKGROUND ART

Traumas or diseases of the spine result in damage to individual vertebrae, intervertebral discs, or combinations thereof Different techniques are used for the surgical treatment, according to the indications, among which is the prosthesis of lost or removed fragments and their stabilization within the spinal column, otherwise called spondylodesis in surgical practice.

It is desirable to develop new and improved technical devices for spinal surgery providing improved functional attributes, increase of success rate, and the further extension of their applications.

Existing approaches include a technique of posterior-spondylodesis [1. Russian Patent 2,076,6541] employing a device consisting of a set of supporting implants that are cylindrical in shape, a stratified implant, and a bracing device, the brace is made of TiNi alloy with thermomechanical shape memory.

Cylindrical implants are positioned into sockets created between adjacent spinous processes of injured vertebral bodies. These are employed as supports between the vertebrae and serve to fix the injured segment of the spine.

The stratified implant is installed into a channel prepared in the cortical laminar layer and arched articular processes. Jointly and in contact with the cylindrical implants, it functions as a support and fixation device. The brace is used to brace the successive spinous processes and cylindrical implants, and it is also a dynamic element assisting in the correction of possible scoliotic deformities of the spine in the injured area.

The disadvantage of this device is its structural complexity and accompanying increased traumatism, the complexity of the operation required, and the high rigidity that results in the immobilization of the spinal segment.

A further device [2. Russian Patent 1,591,9781] for use in the surgical treatment of spinal injuries consists of a cylindrical rod made of porous TiNi alloy and fixing elements in the form of undulating curved clamps made of solid TiNi with shape-memory effect. In order to make the device compact and anatomically consistent, the fixing elements are installed into the longitudinal channels of the rod.

This device is used for the complete replacement of the vertebral body. It is fixed in place with fixing elements whose curved ends have been previously introduced into sockets in the upper segments of the inferior and lower segments of the superior adjacent intact vertebrae. During the installation, the shape-memory effect of the fixing elements is deployed. The disadvantage of this device is its high rigidity, which results in the immobilization of the spinal segment.

Another device [3. Russian Patent 1,526,6751] for the surgical treatment of the spine, which is used for partial or complete replacement of the vertebrae is illustrated in FIG. 1 and consists of a supporting element of cylindrical shape made of porous TiNi alloy, with fixing projections at its ends, one of which is immobile, while the other, at the opposite end, is movable in an axial direction and is provided with a spiral spring made of solid TiNi alloy with shape-memory effect. When performing the prosthesis of the spinal segment, the ends of the device are installed into sockets prepared in the proximal intact bone portion of the spine. The fixing projections prevent potential luxation of the spine at the site of the implantation.

The disadvantage of this device is the rigidity of its structure, which leads to the immobilization of the prosthetic segment.

DISCLOSURE OF THE INVENTION

The technical outcome of the present invention is the provision of mobility in the prosthetic segment of the spine.

In accordance with the invention there is provided a non-fusion, intervertebral, implant device adapted to partially or completely replace an intervertebral disc in the spinal column of a human comprising a resilient body, which body comprises porous TiNi, the body being internally mobile such that the body resiliently expands and contracts in response to variation in forces applied externally on said body.

In another aspect of the invention there is provided an improvement in a surgical method in which an intervertebral disc is replaced by an implant device, the implant device being a device of the invention as defined hereinbefore.

DESCRIPTION OF PREFERRED EMBODIMENTS i) Implant Device

The implant device of the invention may be generally referred to as an artificial disc, since it is to function as a partial or complete replacement for an intervertebral disc. However, while the implant device is employed for the function of an intervertebral disc it need not have a disc shape.

The device is a non-fusion device, which means that the device will not cause a fusion of adjacent vertebral bodies, but will permit the spine to retain its flexibility by permitting movement between the adjacent spinal column members.

A device of the invention may suitably have a body with a structure of layered sheets of porous TiNi, in which adjacent sheets of a plurality of such sheets are in opposed, spaced apart facing relationship.

The structure is preferably an integral unitary structure; this may be achieved, in one embodiment by a body having the form of a rolled sheet of porous TiNi, the rolled sheet having a layered structure with adjacent winds or windings of the roll form being spaced apart.

Thus such a device for the surgical treatment of spinal injures contains a supporting element made of porous TiNi alloy; this element may be made in the form of a rolled sheet with a layered structure, preferably the openings or spaces between the adjacent layers of the roll conform to a ratio of 0.1 to 1.0:1 relative to the thickness of the sheet.

It will be understood that the sheet has a thickness such that it can be readily coiled or rolled on itself to vary the diameter of the roll.

A cylindrical shape of the rolled form is recommended.

A flattened shape of the rolled form is also recommended.

In one preferred embodiment, a suitable porous TiNi alloy in the device of the invention has a porosity of 8 to 90%, and more especially comprises a porous body, in which the porosity extends throughout the body. In particular, the body may be formed with a controllable and variable porosity. On the other hand the invention applies also to other porous TiNi such as that described in S.U. 1381764.

In preferred embodiments, employing the preferred porous TiNi referred to above, the porosity is defined by a network of interconnected passageways extending throughout the alloy; the network exhibits a permeability for fluid material effective to permit complete migration of the fluid material throughout the network; this alloy is elastically deformable.

Preferably the porosity is at least 30% and preferably not more than 70%.

Preferably the permeability is derived from capilliarity in the network of passageways which define the porosity.

This capilliarity may be produced in the alloy by inclusion therein of a large number of pores of fine size which interconnect to produce capillary passages.

Capilliarity is advantageous in that it promotes migration of spinal biological fluids into the network of passageways, and retention of the fluid material in the network, without the need to apply external hydraulic forces.

In general the network has a coefficient of permeability of $2 \times 10^{-13}$ to $2 \times 10^{-5}$, and the permeability is isotropic.

The capilliarity and the isotropic character are, in particular, achieved when the network defining the porosity comprises pores of different pore size, the pore size distribution preferably being as follows:

| Pore Size in Microns | Quantity |
|---|---|
| $10^{-2}$–10 | 5–15% |
| 10–400 | 15–70% |
| 400–1000 | 10–70% |
| above 1000 | remainder to 100%. |

Suitable TiNi alloys for use in the invention are described in WO 99/34845, published Jul. 15, 1999, the teachings of which are incorporated herein by reference.

Pore size is an important factor in tissue or biological aggregate growth. At least some of the pores need to be of a size to permit the development or growth of biological aggregates synthesized from the components of the biological fluid, for example, osteons.

Furthermore, if pore size is increased, the capillary effect decreases.

The medical objective of the vertebral prosthetics is the maximal restoration of spinal functions, namely, the flexible shock-absorbing support of the organism.

The shape of the supporting element or device of the invention has a great impact upon the outcome of the surgery. Suitably it may be cylindrical. The cylindrical shape is more easily fabricated, and simplifies the manipulations of the surgeon both when preparing the socket for implant and during the fixation. In some cases anatomical pecularities and the pathology of the spinal segment will call for an adaptive variation in the shape of the supporting element or device, namely, flattened like the intervertebral discs. The manufacture of such elements is more elaborate, but recent developments in the technology used for processing devices made of porous TiNi alloy have made this realizable.

ii) Titanium-Nickel

The porous titanium-nickel based alloy may suitably comprise 40 to 60%, by atomic weight titanium and 60 to 40%, by atomic weight, nickel to a total of 100%; and more preferably 48 to 52%, by atomic weight, titanium, 48 to 52%, by atomic weight, nickel, less than 2%, by atomic weight, molybdenum, less than 2%, by atomic weight, iron and minor or trace amounts of other elements, to a total of 100%. Desirably the alloy contains each of molybdenum and iron in an amount of more than 0%, by atomic weight and less than 2%, by atomic weight.

Nickel-titanium alloy has significant advantages, as compared with other materials, in biomedical applications such as the present implant device. In particular it displays a high level of inertness or biocompatibility, it has high mechanical durability thus providing longevity when employed in the fabrication of implants.

Bone tissue has an elasticity which renders it resilient to permanent deformity when subjected to stress and vibrations. If material employed in an implant which contacts such bone tissue has different characteristics from the bone tissue it will not meet the requirement for biomechanical compatibility in an implant and longevity will be short. The porous titanium-nickel alloy in the device of the invention is found to display mechanical behaviour very similar to that of bone tissue, thus showing high biomechanical compatibility.

iii) Process

The porous titanium nickel of the implant device is preferably produced with a controlled pore size distribution, as indicated above. In particular the porous titanium nickel may be produced in accordance with the procedures described in the Russian publication "Medical Materials and Implants with Shape Memory Effect" 1998, Tomsk University, p-460 to 463, Gunther V. et al, the teachings of which are incorporated herein by reference. In summary, this alloy can be produced by powder metallurgy method by means of the so-called SHS (Self-Propagating High-Temperature Synthesis) method using two different processes:

Layerwise combustion SHS: Heat is generated by initial ignition. Then thermal conductivity raises the temperature of the neighbouring layers of the substance, thus causing reaction within, and thus resulting in spatial displacement of the reaction zone in the volume. The reaction takes place in a thin layer called the combustion front.

Thermal shock SHS: In this process, the thermal shock is performed by heating a mixture of various powders up to the temperature at which the self supported chemical reaction and heat release effect takes place. Due to the self-heating process the mixture is heated up to higher temperatures, thus the mixture of the powders is converted into alloy.

The two processes are explained more fully in the aforementioned publication of Gunther V. et al and the aforementioned WO 99/34845 published Jul. 15, 1999, both of which are incorporated herein by reference for their teachings of the processes for producing porous TiNi.

BRIEF DESCRIPTION OF DRAWINGS

The invention is illustrated in the accompanying drawings in which.

EXAMPLE

The possibility of achieving the stated technical outcome is illustrated by a test case of the clinical trial use of the implant in the Regional Clinical Hospital (RCH) of the City of Novosibirsk (case no. 2-3576).

Male patient D., 45 years old, was treated in the Department of Neurosurgery of RCH for discogenic myelopathy, medial hernia of disk $C_6$–$C_7$, and tetraparesis.

Computer tomography confirmed posterior medial hernia of the disk $C_6$–$C_7$.

Figure 1:
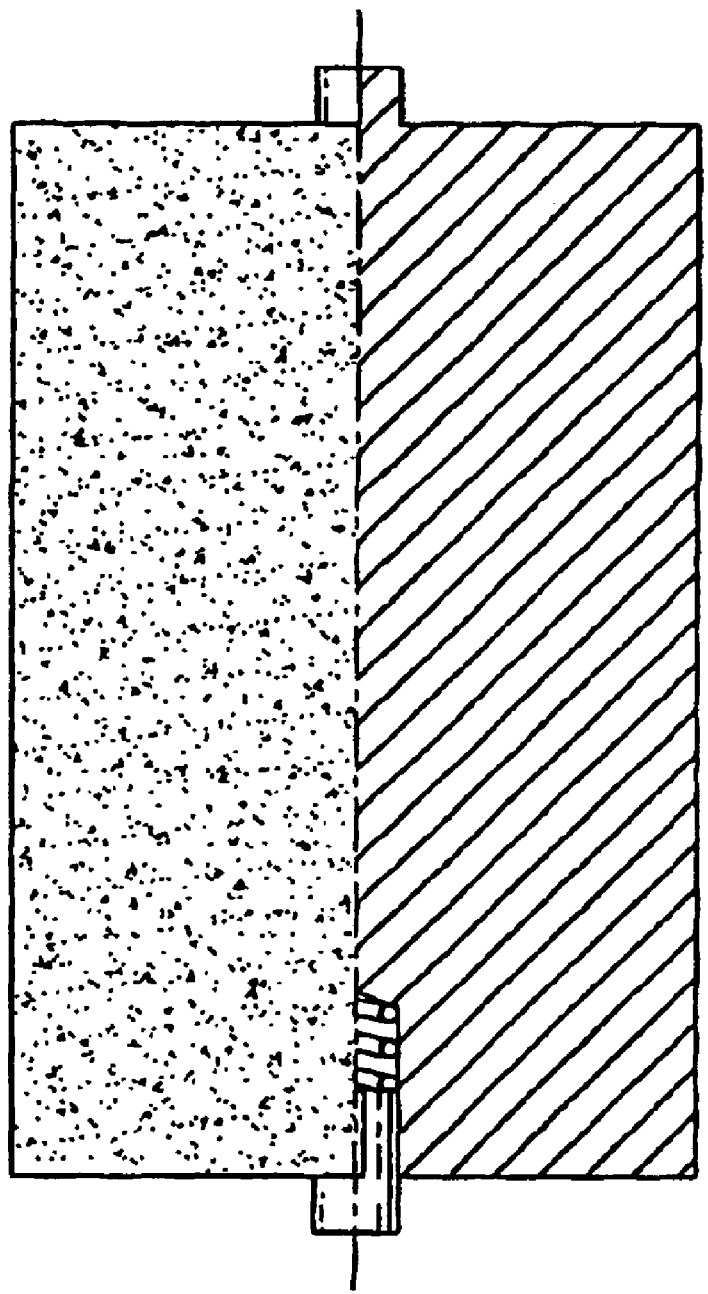
FIG. 1 is a prior art device for the surgical treatment of spinal injuries
Figure 2:
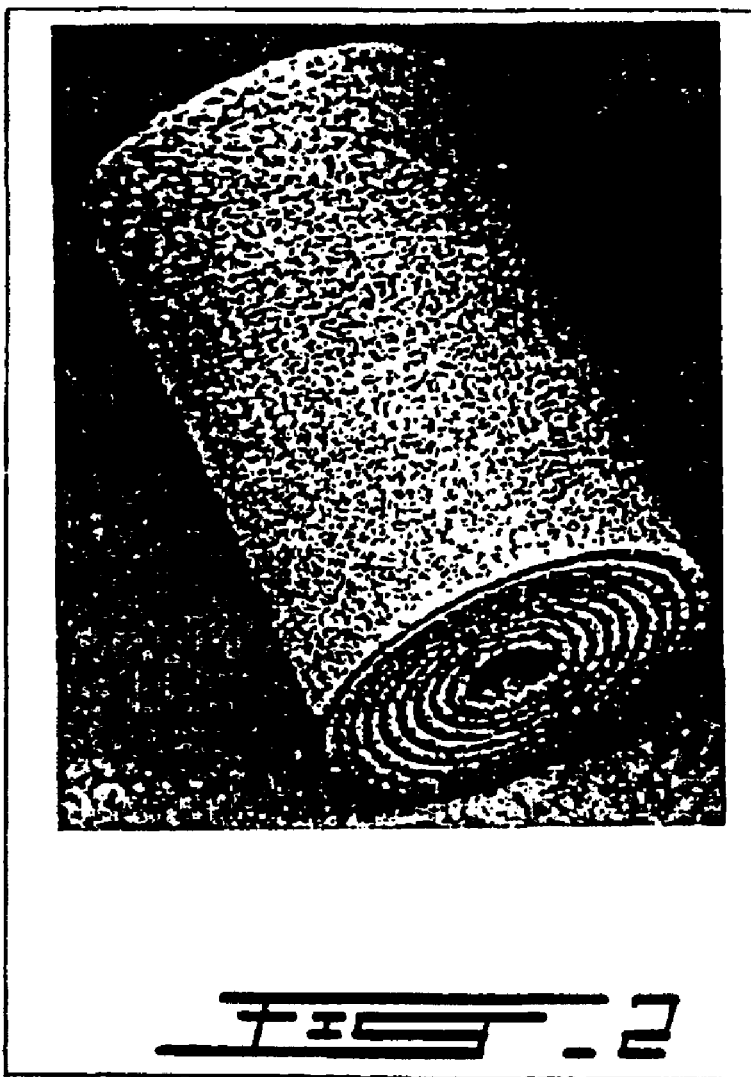
FIG. 2 is a device of the invention for the surgical treatment of spinal injuries.

The patient underwent surgery for anterior interbody spondylodesis using the device of the invention. The device made of porous superelastic TiNi alloy in the shape of a rolled sheet (FIG. 2) with the following dimensions was used: length of the device 20 mm, diameter 18 mm, thickness of the sheet 0.4 mm, opening between the layers 0.2 mm.

The device was used in the following way. After total $C_6$–$C_7$ discectomy, a medial interbody socket with a diameter of 17 mm was created in the bodies of vertebrae $C_6$–$C_7$.

Figure 3A:
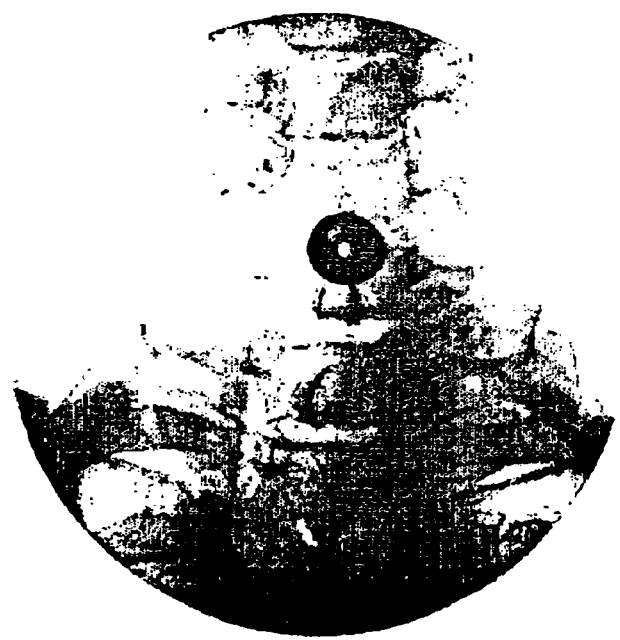
FIGS. 3(a and b) is a Roentgenogram (X-Ray) of the device of the invention implanted into the cervical segment of a patient's spine.
Figure 3B:
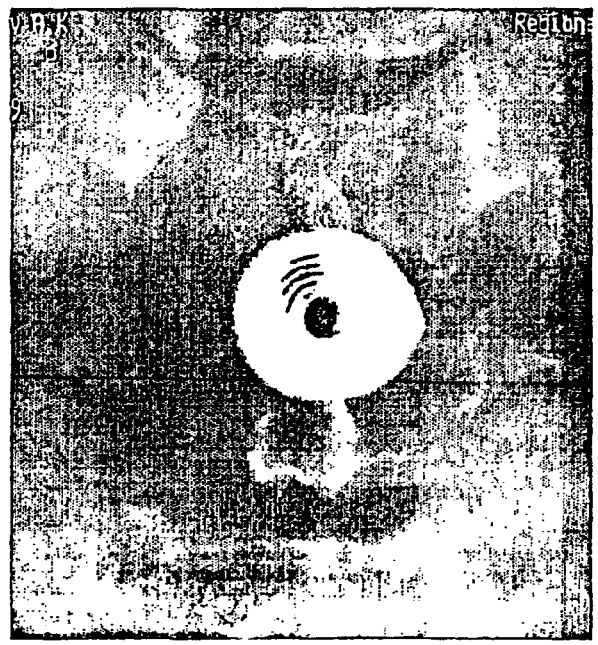

The device, preliminarily sterilized and elastically deformed by coiling the roll to a diameter smaller than 17 mm, was installed into the interbody socket. Under the effect of elasticity and due to the roughness of the surface of the porous structure, the device fixes itself in the osseous socket by uncoiling (FIG. 3). The wound was sutured. The cervical segment of the spine was fixed with a Philadelphia collar. After 2 days the patient was transferred to active status. Positive dynamics in the form of a regression of tetraparesis were observed.

References:
1. Patent of the Russian Federation 6 A 61 B 17/56, 17/70 No. 2076654.
2. Patent of the Russian Federation 5 A 61 F No. 1591978.
3. Patent of the Russian Federation 4 A 61 B 17/60 No. 1526675.

What is claimed is:

1. A non-fusion intervertebral implant device adapted to partially or completely replace an intervertebral disc in the spinal column of a human comprising a resilient body, said resilient body comprising a porous TiNi sheet structure having a porosity defined by a network of interconnected passageways extending through the porous TiNi sheet structure, said body being internally mobile such that the body resiliently expands and contracts in response to variation in forces applied externally on the body, said sheet being in a layered arrangement in which adjacent layers are in opposed spaced apart, facing relationship, with a ratio of spacing between adjacent layers to thickness of the sheet of 0.1 to 1:1.

2. A device according to claim 1, wherein said structure is of a continuous sheet.

3. A device according to claim 1, wherein said structure is an integral unitary structure.

4. A device according to claim 1, wherein said structure has the form of a rolled sheet of porous TiNi in which adjacent windings of the rolled sheet are in said opposed spaced apart, facing relationship.

5. A device according to claim 4, wherein said structure is cylindrical.

6. A device according to claim 4, wherein said structure is in the form of a cylinder flattened at opposed sides.

7. A device according to claim 1, wherein said porous TiNi has a porosity of at least 30% and not more than 70%, said network having a distribution of pore size as follows:

| Pore Size in Microns | Quantity |
| --- | --- |
| $10^{-2}$–10 | 5–15% |
| 10–400 | 15–70% |
| 400–1000 | 10–70% |
| above 1000 | remainder to 100%. |

8. A device according to claim 7, wherein said network exhibits a coefficient of permeability of $2\times10^{-13}$ to $2\times10^{-5}$.

9. A device according to claim 1, wherein said porous TiNi comprises 40 to 60%, by atomic weight, titanium, 40 to 60%, by atomic weight, nickel, less than 2%, by atomic weight, molybdenum less than 2%, by atomic weight, iron and minor amounts of other elements, to a total of 100%.

10. A device according to claim 1, wherein said porous TiNi comprises 48 to 52%, by atomic weight, titanium, 48 to 52%, by atomic weight, nickel, less than 2%, by atomic weight, molybdenum, less than 2%, by atomic weight, iron and minor amounts of other elements, to a total of 100%.

11. In a surgical method in which an intervertebral disc is partially or completely replaced by an implant device, the improvement wherein the implant device is a non-fusion intervertebral implant device adapted to partially or completely replace an intervertebral disc in the spinal column of a human comprising a resilient body, said resilient body comprising a porous TiNi sheet structure having a porosity defined by a network of interconnected passageways extending throughout the porous TiNi sheet structure, said body being internally mobile such that the body resiliently expands and contracts in response to variation in forces applied externally on the body, said sheet being in a layered arrangement in which adjacent layers are in opposed spaced apart, facing relationship, with a ratio of spacing between adjacent layers to thickness of the sheet of 0.1 to 1:1.

12. A method according to claim 11, wherein said porous TiNi has a porosity of at least 30% and not more than 70%, said network having a distribution of pore size as follows:

| Pore Size in Microns | Quantity |
| --- | --- |
| $10^{-2}$–10 | 5–15% |
| 10–400 | 15–70% |
| 400–1000 | 10–70% |
| above 1000 | remainder to 100%. |

13. A method according to claim 11, wherein said porous TiNi comprises 40 to 60%, by atomic weight, titanium, 40 to 60%, by atomic weight, nickel, less than 2%, by atomic weight, molybdenum, less than 2%, by atomic weight, iron and minor amounts of other elements, to a total of 100%.

14. A method according to claim 11, wherein said porous TiNi comprises 48 to 52%, by atomic weight, titanium, 48 to 52%, by atomic weight, nickel, less than 2%, by atomic weight, molybdenum, less than 2%, by atomic weight, iron and minor amounts of other elements, to a total of 100%.

15. A device according to claim 1 wherein said network exhibits a coefficient of permeability of $2\times10^{-13}$ to $2\times10^{-5}$, said passageways having a capilliarity effective to promote migration of spinal fluids into the network and retention of such fluids in the network without application of external hydraulic forces; and said network defining the porosity comprises pores of different pore sizes.

16. A device according to claim 15 wherein said permeability is isotropic.

17. A method according to claim 11 wherein said network exhibits a coefficient of permeability of $2\times10^{-13}$ to $2\times10^{-5}$, said passageways having a capilliarity effective to promote migration of spinal fluids into the network and retention of such fluids in the network without application of external hydraulic forces; and said network defining the porosity comprises pores of different pore sizes.

18. A method according to claim 17 wherein said permeability is isotropic.

19. A method according to claim 11 wherein said structure is a unitary integral structure.

* * * * *